United States Patent [19]

Markezich et al.

[11] 4,312,803

[45] Jan. 26, 1982

[54] THERMALLY STABLE POLYCARBONATE COMPOSITIONS

[75] Inventors: Ronald L. Markezich; Gary L. Freimiller; Walter K. Olander, all of Mt. Vernon, Ind.; Robert J. Axelrod, Glenmont, N.Y.

[73] Assignee: General Electric Company, Mt. Vernon, Ind.

[21] Appl. No.: 21,563

[22] Filed: Mar. 16, 1979

[51] Int. Cl.$^3$ .......................... C07F 9/15; C08K 5/52
[52] U.S. Cl. ...................... 260/45.7 PH; 260/45.8 A; 260/45.8 R; 260/927 R
[58] Field of Search ....... 260/45.8 R, 927 R, 45.7 PH

[56] References Cited

U.S. PATENT DOCUMENTS

| | | | |
|---|---|---|---|
| 2,952,701 | 9/1960 | McConnell et al. | 260/927 R |
| 3,231,531 | 1/1966 | Buckley et al. | 260/45.7 PH |
| 3,305,520 | 2/1967 | Fritz et al. | 260/45.7 PH |
| 3,398,212 | 8/1968 | Jackson, Jr. et al. | 528/125 |
| 3,467,733 | 9/1969 | Dever et al. | 260/927 R |
| 3,476,699 | 11/1969 | Kauder et al. | 260/927 R |
| 3,488,407 | 1/1970 | Schall et al. | 260/927 R |
| 3,737,485 | 6/1973 | Hechenbleikner | 260/45.8 R |
| 3,845,168 | 10/1974 | Guttag | 260/927 R |
| 3,940,367 | 2/1976 | Pelousek et al. | 260/45.8 R |
| 4,064,100 | 12/1977 | Hechenbleikner | 260/927 R |
| 4,066,611 | 1/1978 | Axelrod | 260/927 R |
| 4,088,709 | 5/1978 | Seymour et al. | 260/45.8 R |

*Primary Examiner*—John Kight, II
*Assistant Examiner*—R. A. White
*Attorney, Agent, or Firm*—Martin B. Barancik; William F. Mufatti

[57] ABSTRACT

Thermally stable polycarbonate compositions are obtained by admixing with a high molecular weight aromatic polycarbonate resin a stabilizing amount of a bisphosphite.

2 Claims, No Drawings

THERMALLY STABLE POLYCARBONATE COMPOSITIONS

This invention relates to thermally stable polycarbonate compositions comprising an admixture of an aromatic polycarbonate and a stabilizing amount of a bisphosphite.

BACKGROUND OF THE INVENTION

In the past, much effort has been expended in preparing thermally stable polycarbonate compositions which would be color stable at elevated temperatures and particularly at the high molding temperatures generally employed to prepare molded polycarbonate articles. Many different additives have been found that are quite suitable for rendering polycarbonates heat and color stable. Particularly useful are triorgano phosphites such as are disclosed in U.S. Pat. No. 3,305,520. In addition, U.S. Pat. Nos. 3,729,440 and 3,953,388 disclose thermally stable aromatic polycarbonates containing a phosphinite and an epoxy compound. Further, U.S. Pat. No. 3,794,629 discloses chemically stable aromatic polycarbonates containing oxetane phosphites and U.S. Pat. No. 3,978,020 discloses thermally stable aromatic polycarbonates containing phosphonites which include epoxy compounds.

U.S. Pat. No. 3,509,091 discloses stabilized polycarbonate compositions wherein the stabilizer is a cyclic monophosphite compound. While useful, these cyclic monophosphites have low boiling points so that much of the stabilizer is lost during extrusion of the polycarbonate at the relatively high extrusion temperatures typically employed. Thus, such cyclic monophosphite stabilizers are difficult to process and uneconomical to use as they are generally employed in excess amounts in order to incorporate effective stabilizing amounts in the polycarbonate.

Polycarbonates are also used for producing bottles; however, these bottles become hazy after sterilization in water or exposure to moisture at elevated temperatures. U.S. Pat. No. 3,839,247 discloses a water clear polycarbonate composition which can be used to mold bottles wherein the polycarbonate composition contains an aromatic epoxy or an aliphatic epoxy compound as a stabilizer.

Copending application Ser. No. 957,426, filed Nov. 2, 1978, discloses aromatic polycarbonate compositions containing phosphonite oxetanes; copending application Ser. No. 957,429, filed Nov. 2, 1978, discloses aromatic polycarbonate compositions containing a phosphite oxetane containing a hindered phenol; copending application Ser. No. 957,430, filed Nov. 2, 1978, discloses aromatic polycarbonate compositions containing a phenol phosphite or a hindered phenol phosphite; copending application Ser. No. 957,427, filed Nov. 2, 1978, discloses aromatic polycarbonate compositions containing dioxane phosphites, and, copending application Ser. No. 957,428 filed Nov. 2, 1978 discloses aromatic polycarbonate compositions containing a phosphonite or a phosphonite oxetane each of which contains a hindered phenol; each of these copending applications being assigned to the same assignee as this case.

DESCRIPTION OF THE INVENTION

It has been discovered that when an aromatic polycarbonate is admixed with a bisphosphite; i.e., a diphosphite, the resulting polycarbonate composition has improved thermal stability as exemplified by its resistance to yellowing when subjected to high molding temperatures.

The bisphosphite compounds that can be used in the present invention are represented by the general structure:

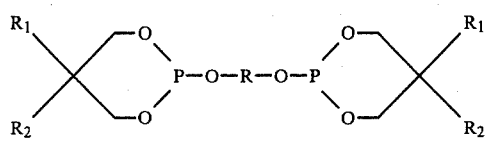

wherein R can be a $C_2$–$C_{36}$ alkyl, a $C_6$–$C_{36}$ aryl, an alkyl aryl of at least $C_7$, and up to about $C_{36}$, and mixtures thereof; and, $R_1$ and $R_2$ can each independently be unsubstituted and halogen substituted alkyl, aryl, cycloalkyl, aralkyl and alkaryl radicals of about $C_1$–$C_{30}$. Typical $R_1$ and $R_2$ substituents are such components as methyl, ethyl, n-propyl, isopropyl, n-butyl, sec-butyl, tertiary butyl, n-amyl, isoamyl, tertiary amyl, n-hexyl, dodecyl, nonyl, and the like; cycloalkyl such as cyclohexyl, 2-methylcyclohexyl, 4-methylcyclohexyl, 2-ethylcyclohexyl, 4-ethylcyclohexyl, 4-isopropylcyclohexyl, and the like; aryl such as phenyl, naphthyl, 2-naphthyl, biphenyl of terphenyl, and the like; aralkyl such as benzyl, phenylethyl, 2-phenylethyl, 1-phenylpropyl, 2-phenylpropyl, and the like; alkaryl such as p-tolyl, m-tolyl, 2,2-xylyl, o-tolyl, p-cumyl, m-cumyl, o-cumyl, mesityl, p-tertiary butylphenyl, and the like; and, haloaryl such as 2-chlorophenyl, 2,4,6-trichlorophenyl, 2,4,6-tribromophenyl, and the like, wherein the substituted portions thereof can be halogen atoms.

The bisphosphite compounds of the invention are admixed with the aromatic polycarbonate in a stabilizing amount which is generally on the order of about 0.005–1.0, preferably 0.01–0.50 and optimumly about 0.02–0.20 weight percent, based upon the weight of the aromatic polycarbonate.

The bisphosphites that can be employed in the practice of this invention can include dialcohols which can be obtained from methane, ethane, propane, isopropane, butane, hexane, pentane, neopentane, decane, dodecane, nonane, and the like, as well as mixtures thereof.

The bisphenols, i.e., dihydric phenols, that can be employed to obtain the bisphosphite compounds of the invention can be the same as those employed to obtain the aromatic polycarbonates of the invention and which are more fully described hereinbelow.

The aromatic polycarbonates that can be employed in the practice of this invention are homopolymers and copolymers and mixtures thereof that are prepared by reacting a dihydric phenol with a carbonate precursor.

The dihydric phenols that can be employed are bisphenols such as bis(4-hydroxyphenyl)methane, 2,2-bis(4-hydroxyphenyl)propane (bisphenol-A), 2,2-bis(4-hydroxy-3-methylphenyl)propane, 4,4-bis(4-hydroxyphenyl)heptane, 2,2-bis(4-hydroxy-3,5-dichlorophenyl)-propane, 2,2-bis(4-hydroxy-3,5-dibromophenyl)propane, etc.; dihydric phenol ethers such as bis(4-hydroxyphenyl)ether, bis(3,5-dichloro-4-hydroxyphenyl)ether, etc.; dihydroxydiphenyls such as p,p'-dihydroxydiphenyl, 3,3'-dichloro-4,4'-dihydroxydiphenyl, etc.; dihydroxyaryl sulfones such as bis(4-hydroxyphenyl)sulfone, bis(3,5-dimethyl-4-hydroxyphenyl)sulfone, etc.; dihydroxy benzenes, resorcinol, hydroquinone, haloand alkyl-substituted dihydroxy benzenes such as 1,4-dihydroxy-2,5-dichlorobenzene, 1,4-dihydroxy-3-methylbenzene, etc.; and dihydroxy diphenyl sulfoxides such as bis(4-hydroxyphenyl)sulfoxide, bis(3,5-dibromo-4-hydroxyphenyl) sulfoxide, etc. A variety of additional dihydric phenols are also available to provide carbonate polymers such as are disclosed in U.S. Pat. Nos. 2,999,835, 3,028,365 and 3,153,008. Also suitable for preparing the aromatic carbonate polymers are copolymers prepared from the above dihydric phenols copolymerized with halogen-containing dihydric phenols such as 2,2-bis(3,5-dichloro-4-hydroxyphenyl)propane, 2,2-bis(3,5-dibromo-4-hydroxyphenyl)propane, etc. It is also possible to employ two or more different dihydric phenols or a copolymer of a dihydric phenol with a glycol or with hydroxy or acid terminated polyester, or with a dibasic acid in the event a carbonate copolymer or interpolymer rather than a homopolymer is desired for use in the preparation of the aromatic polycarbonates of this invention as well as blends of any of the above materials.

The carbonate precursor can be either a carbonyl halide, a carbonate ester or a haloformate. The carbonyl halides which can be employed are carbonyl bromide, carbonyl chloride and mixtures thereof. Typical of the carbonate esters that can be employed are diphenyl carbonate, di-(halophenyl) carbonates such as di-(chlorophenyl) carbonate, di-(bromophenyl) carbonate, di-(trichlorophenyl) carbonate, di-(tribromophenyl) carbonate, etc., di-(alkylphenyl) carbonate such as di-(tolyl) carbonate, etc., di-(naphthyl) carbonate, di-(chloronaphthyl) carbonate, phenyl tolyl carbonate, chlorophenyl chloronaphthyl carbonate, etc., or mixtures thereof. The haloformates suitable for use herein include bishaloformates of dihydric phenols (bischloroformates of hydroquinone, etc.) or glycols (bishaloformates of ethylene glycol, neopentyl glycol, polyethylene glycol, etc.). While other carbonate precursors will occur to those skilled in the art, carbonyl chloride, also known as phosgene, is preferred.

Also included are the polymeric derivatives of a dihydric phenol, a dicarboxylic acid and carbonic acid. These are disclosed in U.S. Pat. No. 3,169,121 which is incorporated herein by reference.

The aromatic polycarbonates of this invention are prepared by employing a molecular weight regulator, an acid acceptor and a catalyst. The molecular weight regulators which can be employed include monohydric phenols such as phenol, chroman-I, paratertiary-butylphenol, parabromophenol, primary and secondary amines, etc. Preferably, phenol is employed as the molecular weight regulator.

A suitable acid acceptor can be either an organic or an inorganic acid acceptor. A suitable organic acid acceptor is a tertiary amine and includes such materials as pyridine, triethylamine, dimethylaniline, tributylamine, etc. The inorganic acid acceptor can be one which can be either a hydroxide, a carbonate, a bicarbonate, or a phosphate of an alkali or alkaline earth metal.

The catalysts which can be employed can be any of the suitable catalysts that aid the polymerization of bisphenol-A with phosgene. Suitable catalysts include tertiary amines such as triethylamine, tripropylamine, N,N-dimethylaniline, quaternary ammonium compounds such as tetraethylammonium bromide, cetyl triethylammonium bromide, tetra-n-heptylammonium iodide, tetra-n-propylammonium bromide, tetramethylammonium chloride, tetramethylammonium hydroxide, tetra-n-butylammonium iodide, benzyltrimethylammonium chloride and quaternary phosphonium compounds such as n-butyl-triphenyl phosphonium bromide and methyltriphenyl phosphonium bromide.

Also included herein are branched polycarbonates wherein a polyfunctional aromatic compound is reacted with the dihydric phenol and carbonate precursor to provide a thermoplastic randomly branched polycarbonate.

These polyfunctional aromatic compounds contain at least three functional groups which are carboxyl, carboxylic anhydride, haloformyl or mixtures thereof. Examples of these polyfunctional aromatic compounds include trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride, and the like. The preferred polyfunctional aromatic compounds are trimellitic anhydride or trimellitic acid, or their haloformyl derivatives.

Also included herein are blends of a linear polycarbonate and a branched polycarbonate.

The bisphosphite stabilizers of the invention can also be employed in combination with triphenylphosphite (TPP). Since TPP is a liquid, the bisphosphites can be readily dissolved in them thereby making the resultant solution easier to handle and incorporate in the aromatic polycarbonates. The triphenylphosphite (TPP) can be employed in amounts of about 5–50% by weight, preferably 15–25% by weight, based upon the bisphosphite employed.

DESCRIPTION OF THE PREFERRED EMBODIMENT

The following examples are set forth to more clearly illustrate the invention. Unless otherwise specified, parts or percents are by weight.

EXAMPLE 1

Preparation of 2,2-Dimethyl-1,3-propanediol bis(neopentyl phosphite)

This phosphite can be prepared by the known reaction of 2,2-dimethyl-1,3-propanediol with phosphorous trichloride as described in *Journal of Organic Chemistry* (24), 630–635, (1959) which is incorporated herein by reference. Alternatively, known transesterification processes such as disclosed in *Organic Phosphorous Compounds*, Vol. 4, edited by G. M. Kosolapoff and L. Maier, (1972), pp. 255–462, and incorporated herein by reference can also be used to react triphenylphosphite (TPP) with 2,2-dimethyl-1,3-propanediol. The reaction between triphenylphosphite and 2,2-dimethyl-1,3-propanediol with distillation of the phenol as it is formed affords the bisphosphite. This bisphosphite was then distilled at 118°–124° C. at 0.1 mm Hg to give a colorless material which solidifies to a colorless solid on standing (m.p. 44°–46° C.). The proton Nuclear Magnetic Resonance (NMR) spectrum showed the methyl protons at 0.73, 1.0 and 1.27 δ (18.1 hydrogens) and the methylene protons at 3.27, 3.57 and 4.13 δ (11.9 hydrogens). The bisphosphite had the following structure:

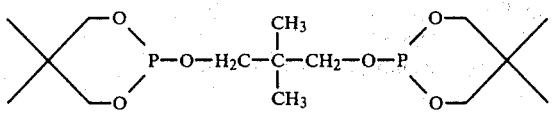

EXAMPLE 2

Preparation of a new bisphosphite:

Bisphenol-A-bis(neopentyl phosphite)

A mixture of 272 g (1.2 mole) of phenyl neopentyl phosphite, 126 g (0.55 mole) of bisphenol-A (BPA) and 1 g of sodium methoxide were heated together in a round-bottom flask. The temperature of the reaction vessel was raised to 130° C. and a vacuum was applied. Phenol was distilled over at 90° C. head temperature at 35 mm. The temperature was raised slowly to 160° C. and the vacuum increased to 0.2 mm Hg to remove any remaining phenol and unreacted phenyl neopentyl phosphite. The proton NMR spectrum of the product recovered showed the methyl protons at 0.77, 1.30 and 1.65 δ (18.1 hydrogens), the methylene protons at 3.67 and 4.30 δ (7.2 hydrogens) and the aromatic protons from 6.7–7.3 δ (8.7 hydrogens). This bisphosphite had the following structure:

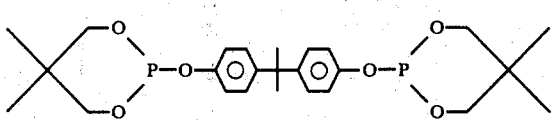

EXAMPLE 3

Preparation of a new bisphosphite:

Tetramethyl-bisphenol-A-bis(neopentyl phosphite)

A mixture of 216 g (0.95 mole) of phenyl neopentyl phosphite, 134 g (0.47 mole) of tetramethyl-bisphenol-A, and 1 g of sodium methoxide were heated together in a round-bottom flask. The temperature of the reaction vessel was raised to 130° C. and a vacuum was applied. Phenol was distilled over a head temperature of 90° C. at 35 mm Hg. The temperature was raised slowly to 160° C. and the vacuum increased to 0.2 mm Hg to remove any phenol and unreacted phenyl neopentyl phosphite. The proton NMR spectrum of the product obtained showed the methyl protons at 0.77, 1.30, 1.60, 2.17 and 2.27 δ (30.8 hydrogens), the methylene protons at 3.37 and 4.43 δ (7.1 hydrogens), and the aromatic protons at 6.83 δ (4.2 hydrogens). This bisphosphite had the following structure:

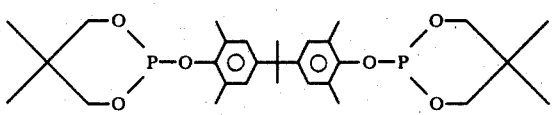

EXAMPLE 4

A polycarbonate composition of a homopolymer of 2,2-bis(4-hydroxyphenyl)propane (bisphenol-A) was prepared by reacting essentially equimolar amounts of bisphenol-A and phosgene in an organic medium with triethylamine, sodium hydroxide and phenol under standard conditions and was mixed with the bisphosphite stabilizers shown in Table I plus a trade amount of a commercially obtained blue pigment by tumbling the ingredients in a laboratory tumbler. This mixture was then fed to an extruder, which extruder was operated at about 500° F., and the extruded strands chopped into pellets. The pellets were then injection molded at 600° F. and 680° F. into test samples of about 3 inches by 2 inches by ⅛ inch thick. Thermal stability to discoloration of the test samples was measured in accordance with ASTM Yellowness Index (YI) Test D1925 on samples molded at 600° F. and 680° F. The results obtained are set forth in Table I below wherein "Control" identifies a polycarbonate sample without stabilizer and having an I.V. of 0.49 dl/g.

TABLE I

| | | Thermal Stability | |
| | | YI of Test Samples Molded At | |
| Stabilizer | Amount (wt %) | 600° F. | 680° F. |
| --- | --- | --- | --- |
| Control | — | 4.1 | 10.3 |
| A* | 0.1 | 2.2 | 6.9 |
| Example 1 | 0.02 | 2.3 | 3.9 |
| Example 1 | 0.04 | 1.7 | 3.7 |
| Example 2 | 0.025 | 2.8 | 6.3 |
| Example 3 | 0.03 | 3.4 | 7.8 |

*Stabilizer as disclosed in German Pat. No. 1,694,285 and referred to in U.S. Pat. No. 3,794,629:
1 part octyldiphenyl phosphite
2 parts 3,4-epoxycyclohexylmethyl-3,4-epoxycyclohexane carboxylate The test samples molded at 680° F. were subjected to accelerated heat aging by placing them in an oven at 140° C. for periods of 1 and 2 weeks. The results obtained are shown in Table II below wherein the YI is shown as the difference; i.e., ΔYI, over the initial YI of test samples molded at 680° F.

TABLE II

| | | ΔYI of Heat Aged 680° F. Molded Test Samples After | |
| Stabilizer | Amount (wt %) | 1 Week | 2 Weeks |
| --- | --- | --- | --- |
| Control | — | 8.1 | 13.2 |
| A | 0.1 | 11.6 | 18.7 |
| Example 1 | 0.02 | 8.5 | 14.6 |
| Example 1 | 0.04 | 9.7 | 16.4 |
| Example 2 | 0.025 | 2.5 | 5.1 |
| Example 3 | 0.03 | 3.6 | 6.7 |

From the results shown in Tables I and II above, it can be seen that the Example 1 stabilizer imparts better thermal stability than stabilizer A. While the Example 2 and 3 stabilizers also imparted improved thermal stability over stabilizer A, they were not as good as the Example 1 stabilizer. However, when the samples were subjected to accelerated heat aging (Table II), the Example 2 and 3 stabilizers performed better than both stabilizer A and Example 1 stabilizer.

EXAMPLE 5

Following the procedures of Example 4, additional test samples were obtained including a mixture of a bisphosphite of the invention with triphenylphosphite. The results obtained are shown in Table III below wherein TPP identifies triphenylphosphite.

TABLE III

| | | Thermal Stability | |
| | | YI of Test Samples Molded At: | |
| Stabilizer | Amount (wt %) | 600° F. | 680° F. |
| --- | --- | --- | --- |
| A 20 wt % TPP | 0.1 | 2.4 | 6.7 |

TABLE III-continued

| Stabilizer | Amount (wt %) | Thermal Stability YI of Test Samples Molded At: 600° F. | 680° F. |
|---|---|---|---|
| 80 wt % Example 1 | 0.025 | 2.1 | 5.0 |
| 20 wt % TPP 80 wt % Example 1 | 0.05 | 1.9 | 5.0 |
| Example 1 | 0.02 | 2.3 | 6.1 |
| Example 1 | 0.04 | 1.8 | 5.0 |

The test samples molded at 680° F. were again subjected to accelerated heat aging by placing them in an oven at 140° C. as described in Example 4 and the results obtained are shown in Table IV below.

TABLE IV

| Stabilizer | Amount (wt %) | ΔYI of Heat Aged 680° F. Molded Test Samples After 1 Week | 2 Weeks |
|---|---|---|---|
| A | 0.1 | 12.6 | 18.9 |
| 20 wt % TPP 80 wt % Example 1 | 0.025 | 1.2 | 2.8 |
| 20 wt % TPP 80 wt % Example 1 | 0.05 | 0.7 | 2.4 |

The results in Tables III and IV reveal that the stabilizer combination of TPP and Example 1 impart improved thermal stability over stabilizer A and stabilizer of Example 1 and also significantly improves heat aging stability.

What is claimed is:

1. A bisphosphite having the stucture:

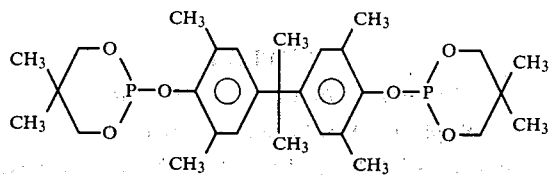

2. A thermally stable aromatic polycarbonate composition comprising an admixture of (1) polymer consisting essentially of a high molecular weight aromatic polycarbonate and (2) a thermal stabilizing amount of about 0.005–1.0 weight percent based upon the weight of the polycarbonate of a bisphosphite having the structure:

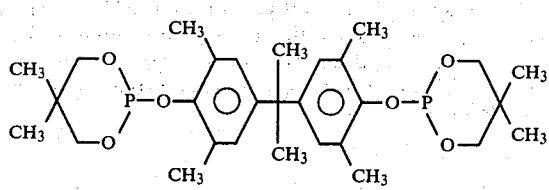

* * * * *